US006618465B2

(12) United States Patent
Mohr et al.

(10) Patent No.: US 6,618,465 B2
(45) Date of Patent: Sep. 9, 2003

(54) X-RAY SHIELDING SYSTEM AND SHIELDED DIGITAL RADIOGRAPHIC INSPECTION SYSTEM AND METHOD

(75) Inventors: Gregory Alan Mohr, Scotia, NY (US); Clifford Bueno, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/683,038

(22) Filed: Nov. 12, 2001

(65) Prior Publication Data

US 2003/0091145 A1 May 15, 2003

(51) Int. Cl.[7] ............................................... G01B 15/06
(52) U.S. Cl. .......................... 378/58; 378/59; 378/146; 378/147; 378/150; 378/160; 378/203
(58) Field of Search .............................. 378/57, 58, 59, 378/60, 146, 147, 150, 160, 203

(56) References Cited

U.S. PATENT DOCUMENTS

| | | | | |
|---|---|---|---|---|
| 4,926,452 A | | 5/1990 | Baker et al. ................... 378/22 |
| 5,014,293 A | * | 5/1991 | Boyd et al. ................... 378/197 |
| 5,237,598 A | * | 8/1993 | Albert ........................ 378/98.6 |
| 5,259,012 A | | 11/1993 | Baker et al. ................... 378/21 |
| 5,493,596 A | * | 2/1996 | Annis .......................... 378/57 |
| 5,524,038 A | | 6/1996 | Fong ............................. 378/4 |
| 5,764,683 A | * | 6/1998 | Swift et al. .................... 378/57 |
| 6,151,381 A | * | 11/2000 | Grodzins et al. ............. 378/90 |
| 6,192,101 B1 | * | 2/2001 | Grodzins ...................... 378/55 |
| 6,229,872 B1 | * | 5/2001 | Amos .......................... 378/58 |
| 6,272,206 B1 | * | 8/2001 | Bjorkholm ................... 378/146 |
| 6,442,233 B1 | * | 8/2002 | Grodzins et al. ............. 378/57 |
| 6,466,643 B1 | * | 10/2002 | Bueno et al. ................. 378/58 |

OTHER PUBLICATIONS

U.S. patent application No. 09/643,688, entitled "High Speed Digital Radiographic Inspection of Aircraft Fuselges" (RD–27780).
U.S. patent application No. 09/770,986, entitled "Method and Apparatus for Localized Digital Radiographic Inspection" (RD–28243).

* cited by examiner

Primary Examiner—Drew A. Dunn
Assistant Examiner—Allen C Ho
(74) Attorney, Agent, or Firm—Penny A. Clarke; Patrick K. Patnode

(57) ABSTRACT

An x-ray shielding system includes a beam controller configured to surround an x-ray source and includes a detector shield configured to position behind an x-ray detector. The beam controller includes a source shield and an aperture. The source shield and the detector shield are adapted to block x-rays, and the aperture is adapted to transmit x-rays. A shielded digital radiographic inspection system includes the x-ray source and the beam controller surrounding the x-ray source. The beam controller includes the source shield and the aperture. The aperture is configured to rotate around the x-ray source. The inspection system further includes a digital x-ray detector positioned radially outward from the x-ray source and facing the aperture. The digital x-ray detector is configured to be movable along an orbit around the x-ray source. The inspection system further includes the detector shield configured to be movable with and positioned behind the digital x-ray detector.

32 Claims, 8 Drawing Sheets

X-RAY SHIELDING SYSTEM AND SHIELDED DIGITAL RADIOGRAPHIC INSPECTION SYSTEM AND METHOD

BACKGROUND OF INVENTION

The invention relates generally to an x-ray shielding system for automated digital radiographic inspection and, more particularly, to an x-ray shielding system for automated digital radiographic inspection of aircraft components.

Aircraft components, such as aircraft fuselage frames, are repeatedly inspected during the life of an aircraft, to detect potentially damaging defects. Presently, aircraft fuselage frames are inspected visually, which requires that the insulation first be removed from the frame. The exposed fuselage frame is then examined visually, with mirrors being used to inspect portions that are difficult to access. However, visual inspection has several drawbacks. First, only large cracks (at least 5 cm in length) are reliably seen, whereas it would be desirable to detect cracks as small as about 1 cm in length. Second, it is difficult to quantify and record the cracks that are visually detected. Third, visual crack inspection is subject to an inspector fatigue factor. Fourth, improper reinstallation of the insulation can introduce moisture condensation, which can lead to corrosion. Moreover, this procedure is time and labor intensive, with a typical inspection period of about five-person days for commercial aircraft, in addition to the labor required to disassemble and reassemble the aircraft interior.

X-ray imaging provides a useful tool for avoiding many of the problems associated with the visual inspection of fuselage frames. Presently, certain areas of the fuselage are examined using x-ray film, and an x-ray source is placed in the fuselage to expose the film. This x-ray imaging method is potentially advantageous relative to visual inspection, in that the insulation need not be removed, small cracks (on the order of 1 cm in length) can be detected, the inspector fatigue factor is eliminated, and the inspection time is reduced. However, due to the large size of aircraft components, powerful x-ray sources are employed, for example on the order of one to one hundred Rad per minute (1–100 R/min). Safety considerations usually dictate that the area around the aircraft be cleared of personnel while x-ray inspections are performed, preventing the concurrent performance of other maintenance activities. In addition, the use of x-ray film is cumbersome, producing x-ray images that are difficult to store and to systematically analyze.

SUMMARY OF INVENTION

Accordingly, it would be desirable to employ digital radiography to image the aircraft fuselage and other aircraft components. Advantageously, this would provide x-ray images that are conveniently stored and analyzed in digital form. However, digital radiography is subject to the radiation exposure concerns discussed above. In addition, digital radiography necessitates moving the x-ray source and an x-ray detector around the aircraft component to image the large components. This, in turn, would require repeated operator intervention. Accordingly, it would be desirable to provide a shielded digital radiographic inspection system for imaging aircraft components that provides additional protections against exposure to harmful radiation.

Briefly, in accordance with one embodiment of the present invention, an x-ray shielding system includes a beam controller configured to surround an x-ray source. The beam controller includes a source shield and an aperture. The x-ray shielding system further includes a detector shield configured to position behind an x-ray detector. The source shield and the detector shield are adapted to block x-rays, and the aperture is adapted to transmit x-rays.

In accordance with another embodiment, a shielded digital radiographic inspection system includes the x-ray source and the beam controller surrounding the x-ray source. The beam controller includes the source shield and the aperture. The beam controller is configured to rotate the aperture around the x-ray source. The inspection system further includes a digital x-ray detector positioned radially outward from the x-ray source and facing the aperture. The digital x-ray detector is configured to be movable along an orbit around the x-ray source. The inspection system further includes the detector shield configured to be movable with the digital x-ray detector and positioned behind the digital x-ray detector.

In accordance with a method embodiment, a shielded digital radiographic inspection method for imaging an aircraft component includes surrounding the x-ray source with the beam controller to produce a collimated x-ray beam through the aperture of the beam controller. The method further includes shielding a back side of a digital x-ray detector to reduce x-ray flux behind the digital x-ray detector, the digital x-ray detector being positioned radially outward from the x-ray source, outside the aircraft component, and facing the aperture. The method further includes imaging a portion of the aircraft component. The imaging includes activating the x-ray source and collecting an image with the digital x-ray detector. The method also includes rotating the aperture around the x-ray source to a subsequent aperture orientation and moving the digital x-ray detector along an orbit around the x-ray source to a subsequent detector position facing the aperture. The rotation of the aperture, the motion of the digital x-ray detector, and the imaging are repeated for a plurality of aperture orientations and detector positions to obtain a plurality of images of an annular portion of the aircraft component.

BRIEF DESCRIPTION OF DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
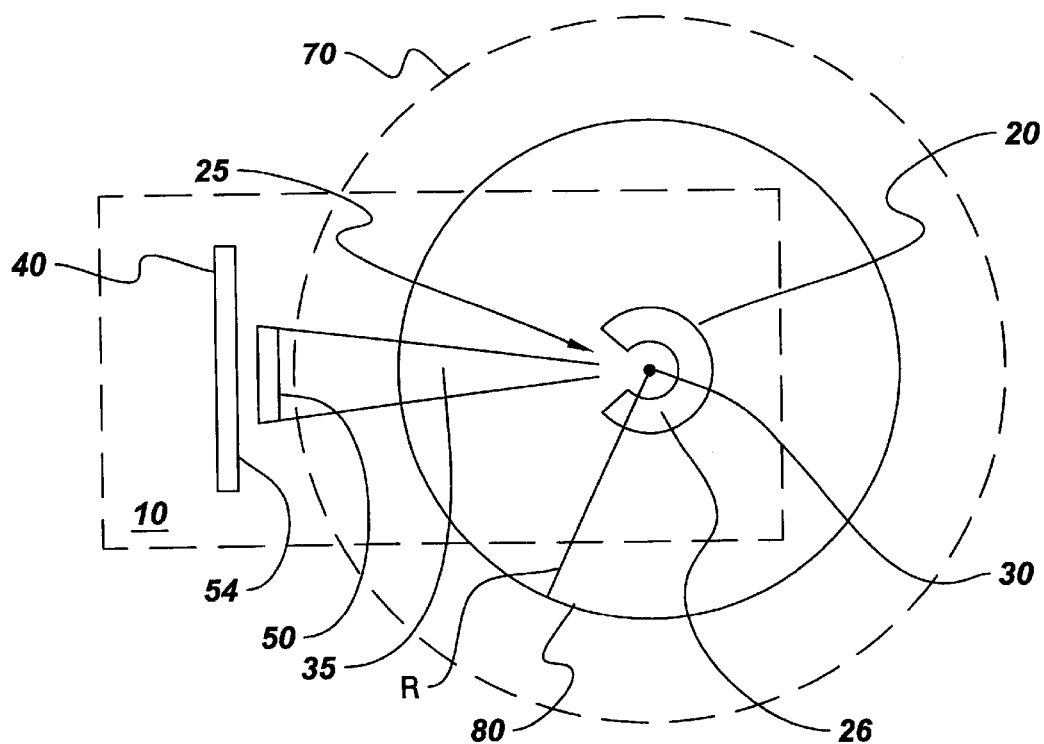
FIG. 1 illustrates an x-ray shielding system embodiment of the invention, in cross-sectional view.
Figure 2:
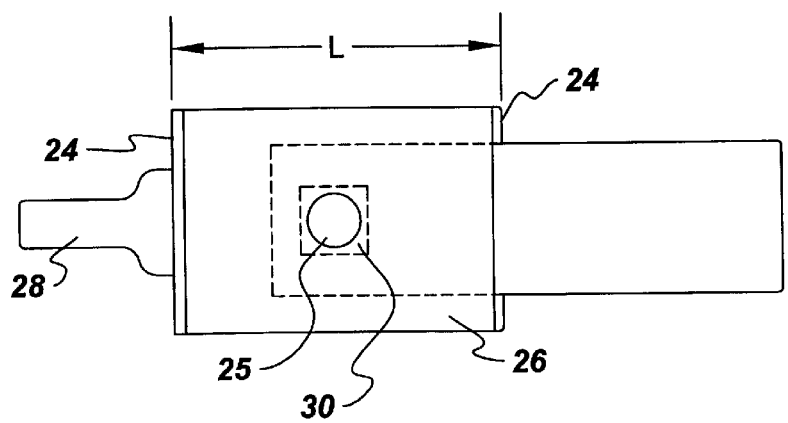
FIG. 2 illustrates the x-ray shielding system of FIG. 1 in side view, with a rotatably mounted beam controller.

An x-ray shielding system 10 embodiment of the invention includes a beam controller 20 configured to surround an x-ray source 30, as illustrated in FIG. 1, in cross-sectional view, and in FIG. 2, in a side view. An exemplary x-ray source is a panoramic x-ray tube powered by a high voltage power supply (not shown). Panoramic x-ray tubes emit radiation with a broad angular distribution, for example in excess of about sixty degrees. However, the x-ray shielding system is not limited to use with any specific type of x-ray source.

The beam controller 20 includes a source shield 26 and an aperture 25, as exemplarily illustrated in FIG. 1. By the phrase "surrounds the x-ray source 30" used above, it is meant that the source shield extends around a circumference of the x-ray source to produce a collimated beam through the aperture. The source shield is adapted to block x-rays emitted by the source. Here, the phrase "adapted to block xrays" means that the source shield comprises a material that blocks x-rays, either by attenuation or absorption. One exemplary beam controller includes sides 24, as illustrated in FIG. 2. The sides extend from the source shield to the x-ray source, further reducing the radiation field 35 by blocking x-rays incident on the sides. Preferably, the source shield and the sides are formed from a high density, high atomic number material, such as lead, tungsten, depleted uranium, or combinations thereof. X-rays are transmitted through the aperture. In this manner, the beam controller controls the radiation field 35, as illustrated in FIG. 1.

Figure 4:
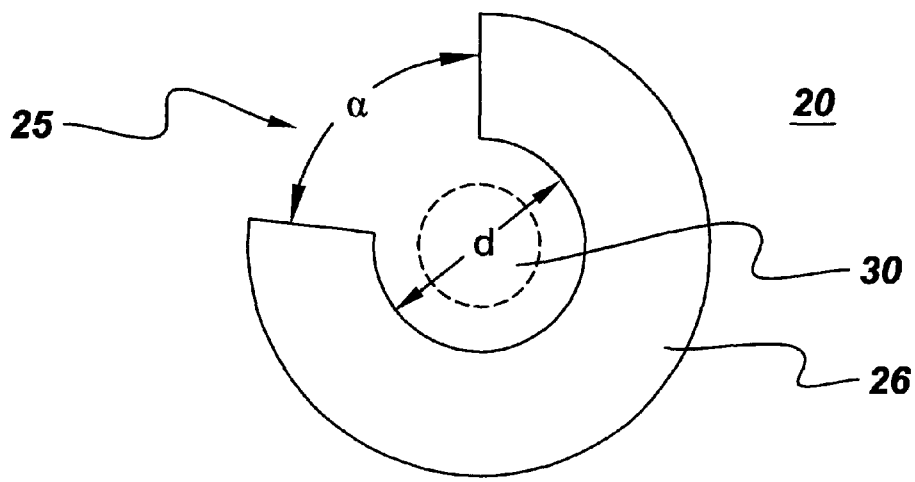
FIG. 4 depicts the beam controller of FIG. 1.

The length L of the beam controller, which is indicated in FIG. 2, depends upon the dimensions of the x-ray source 30. However, an exemplary length L of about 5 cm to about 10 cm generally suffices to shield most of the x-rays emitted by the source. Similarly, the inner diameter d of the beam controller, which is indicated in FIG. 4, varies depending on the diameter of the x-ray source. For example, a beam controller inner diameter of about 5 to about 10 cm accommodates a rod-anode x-ray tube, whereas an inner diameter of about 15 cm to about 30 cm accommodates larger diameter conventional x-ray sources. The x-ray shielding system is not limited to a specific length nor to a specific inner diameter of the beam controller.

The angle encompassed by the aperture 25, represented by reference symbol $\alpha$ in FIG. 4, varies based on the geometry of the configuration of the x-ray source 30, the detector 50, and the beam controller 20. According to one embodiment of the x-ray shielding system 10, the aperture angle $\alpha$ is configured such that the radiation field 35 approximately coincides with the area of the detector 50 at the detector, as shown in FIG. 1. By "approximately coincides," it is meant that the radiation field is incident on at least about 85% of the area of the detector and that at least about 85% of the radiation field is incident on the detector. Thus, for an exemplary distance between the detector and the x-ray source of about 180 cm and an exemplary detector width of about 20 cm, the corresponding aperture angle $\alpha$ would be about 7°. However, both the area of the detector and the radius of the component (and hence the distance between the x-ray source and the detector) will vary from application to application. Accordingly, the x-ray shielding system is not limited to a specific aperture angle $\alpha$. The x-ray shielding system further includes a detector shield 40 configured to position behind an x-ray detector 50. The phrase "behind the x-ray detector" means that the detector is positioned between the x-ray source 30 and the detector shield, as shown in FIG. 1. The detector is positioned outside the hollow component 80 being inspected, as indicated in FIG. 1. By situating the detector and the x-ray source on opposite sides of the hollow component, radiation emitted by the x-ray source irradiates the portion of the hollow component being inspected and subsequently impinges upon the detector. The detector shield 40 is adapted to block x-rays, either by attenuation or absorption, which penetrate or bypass the detector. Preferably, the detector shield is formed from a high density, high atomic number material, such as lead, tungsten, depleted uranium, or combinations thereof. In this manner, the detector shield further reduces the possibility of exposure of aircraft maintenance personnel to errant x-rays.

Figure 3:
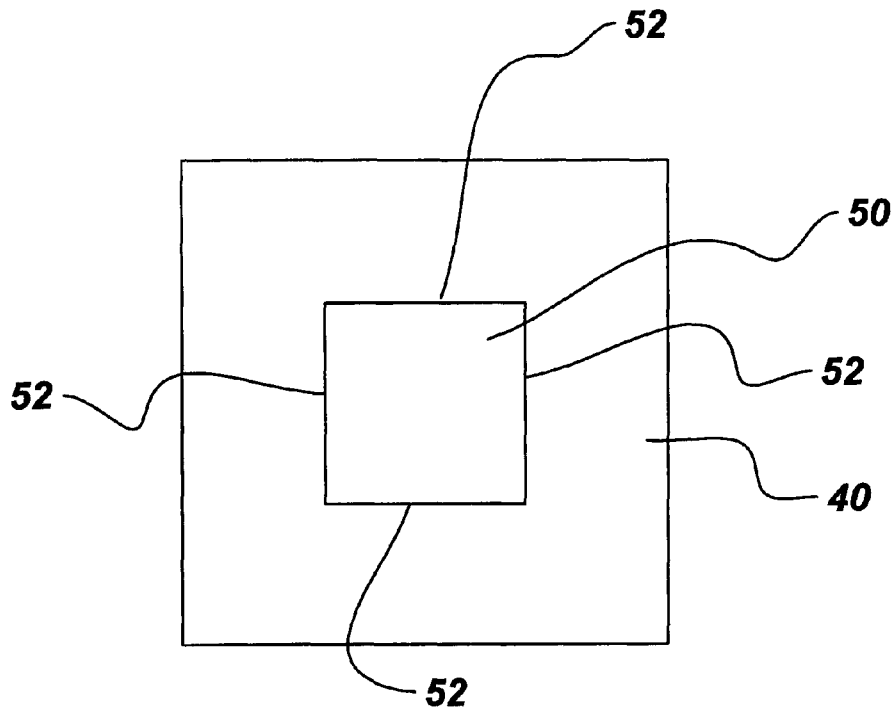
FIG. 3 depicts a detector shield positioned behind a detector.

To block radiation that does not strike the detector, in one embodiment of the x-ray shielding system 10, the detector shield 40 extends beyond the edges 52 of the detector 50, as exemplary shown in FIG. 3. In one example, the detector shield extends at least about 10 cm beyond the detector along each edge of the detector. According to another example, the detector shield extends at least about 50 cm beyond the detector along each edge of the detector. Exemplary detector dimensions are about 20 cm by about 25 cm. Accordingly, exemplary detector shield dimensions for these detector dimensions are about 35 cm by about 35 cm and about 75 cm by about 75 cm.

According to a more specific embodiment, the source shield 26 and the detector shield 40 are thick enough that incident x-rays do not pass through the shields. For shields formed from the above discussed high density, high atomic number materials, a shield thickness of about 0.3 cm to about 1.2 cm, and more particularly of about 0.3 cm to about 0.6 cm, effectively blocks x-rays with energies of about 100 kV or less.

According to one embodiment, the detector 50 is configured to be movable along an orbit 70 around the x-ray source 30. An exemplary detector is moved using a rail system that tracks the path of the radiation field 35 around the orbit 70, as disclosed in commonly assigned, copending U.S. patent application Ser. No. 09/643,688, entitled "High Speed Digital Radiographic Inspection of Aircraft Fuselages," which is hereby incorporated by reference in its entirety. A second exemplary detector is moved using an X-Y scanning device that includes a frame having four rails, as disclosed in commonly assigned, copending U.S. patent application Ser. No. 09/770,986, entitled "Method and Apparatus for Localized Digital Radiographic Inspection," which is hereby incorporated by reference in its entirety. However, these configurations are mentioned by way of example only and are not intended to limit the x-ray shielding system. Further, the detector shield 40 is configured to be movable with the detector such that the detector shield remains positioned behind the x-ray detector at all points along the orbit. An exemplary detector shield is attached to the back 54 of the x-ray detector, such that the detector shield moves with the x-ray detector. In this manner, x-ray leakage is reduced.

Figure 5:
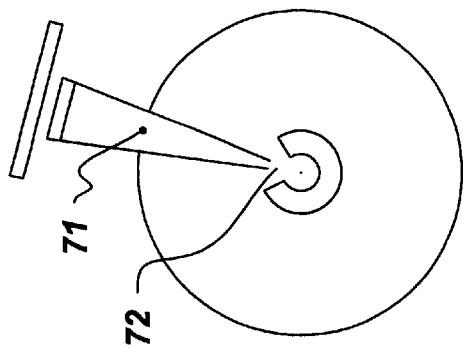
FIG. 5 illustrates synchronization of a beam controller with a detector.
Figure 5:
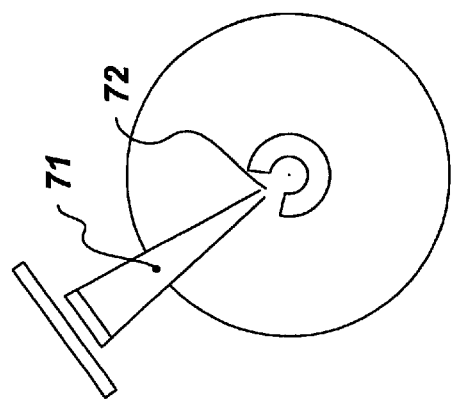
Figure 5:
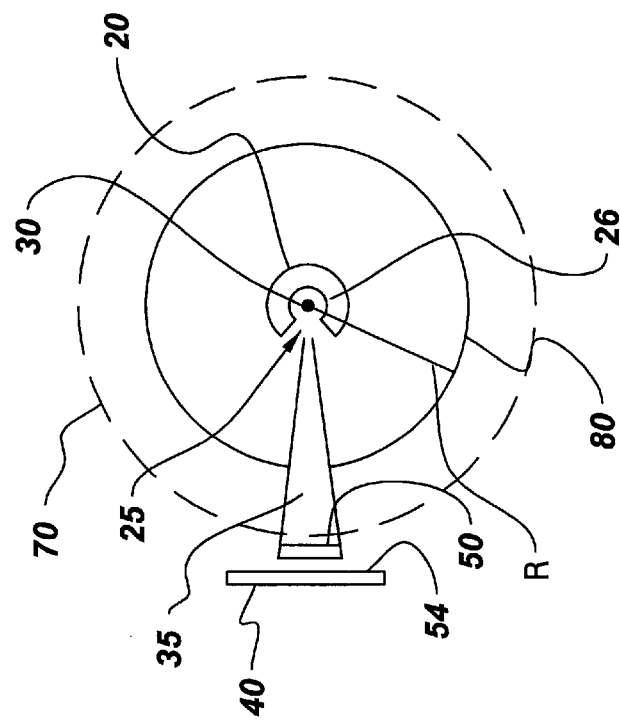

According to this embodiment, the beam controller 20 is configured to rotate the aperture 25 around the x-ray source 30. In one example, the beam controller 20 is configured to rotate around the x-ray source 30. Alternatively, the beam controller is fixed to the x-ray source, and the beam controller and the x-ray source are collectively rotatably mounted, for rotating the aperture as shown in FIG. 5. A rotation device 28 for rotating the beam controller is schematically indicated in FIG. 2. An exemplary rotation device includes a motor (not shown), such as a stepper or servo motor, and a connector (not shown) for connecting the motor to the beam controller. Exemplary connectors include mechanical and electrical connectors. However, there are numerous manners of rotatably mounting the beam controller, and those skilled in the art will recognize that the exemplary rotation device is presented by way of example only. By rotating the aperture, the radiation field 35 illuminates an annulus 80 (shown in cross-sectional view in FIG. 1) of a hollow component, also indicated by reference numeral 80, being inspected. In this manner, the component can be scanned by the x-ray source, without requiring operator intervention, thereby reducing the possibility of radiation exposure of maintenance personnel.

Although FIGS. 1 and 5 depict the radiation field 35 as being directed radially toward the hollow component 80, those skilled in the art will recognize that the position of the x-ray source 30 and the beam controller 20 need not be cylindrically symmetric relative to the hollow component. Rather, the x-ray source and the beam controller can also be oriented such that the radiation field impinges upon the hollow component at a complex angle, to better image certain features of the hollow component, such as flanges or brackets in an airframe structure.

In order to perform x-ray imaging of the component at each detection point along the orbit, the beam controller 20 is adapted to rotate the aperture 25 in synchronicity with the detector 50. In this manner, the rotation of the detector and the aperture are coordinated such that the aperture 25 faces the detector at each imaging position 71 during imaging, as illustrated in FIG. 5. Rotation of the aperture can be synchronized with the movement of the detector in a number of ways. For example, a rotation speed for the aperture can be controlled such that the aperture continuously faces the detector throughout its rotation. Alternatively, the timing of the imaging can be selected such that the aperture faces the detector during imaging. One example of the latter manner of synchronization includes moving the detector to a subsequent position and rotating the aperture, either at a different time or a different angular speed. After the aperture reaches a subsequent orientation, such that the radiation field 35 coincides with the detector, imaging commences at the subsequent position.

In order to rotate the aperture 25 around the x-ray source 30, either the beam controller rotates relative to the x-ray source or the beam controller and the x-ray source rotate collectively. More specifically, for the former configuration, the x-ray source remains fixed, while the beam controller rotates around the x-ray source.

For the second configuration, the beam controller 20 is fixed relative to the x-ray source 30. For example, the beam controller is attached to the x-ray source by mechanical (e.g., screws) or adhesive (e.g., glue) means. Alternatively, the beam controller can be welded to the x-ray source or can be integrally formed with the x-ray source. Moreover, for this configuration the beam controller and x-ray source are collectively rotatably mounted, such that the beam controller and the x-ray source rotate as a single unit irradiating the annulus 80 of the hollow component (also indicated by reference numeral 80) with the radiation field 35. For this configuration, the rotation device 28, which is exemplarily illustrated in FIG. 2, can be connected either to the beam controller or to the x-ray source. Advantageously, this configuration permits imaging the component without requiring operator intervention. Moreover, this configuration provides similar radiation protection advantages for implementations where the x-ray source does not produce an axially symmetric field and allows adaptation to instances where multiple complex angles are required to inspect various regions of hollow components with complex geometry, such as flanges or brackets in airframe structures.

According to another embodiment, the aperture is a variable size aperture (indicated by reference numeral 60), providing an adjustable aperture angle $\alpha$. An exemplary adjustable aperture angle $\alpha$ is adjustable between about 0 degrees (i.e., no x-rays escape from the beam controller) and about 90 degrees. For example, for a distance between the x-ray source 30 and the aircraft of about 25 cm and for a detector about 41 cm in length, an aperture angle of about 80 degrees is configured to provide a radiation field that covers the detector.

Figure 11:
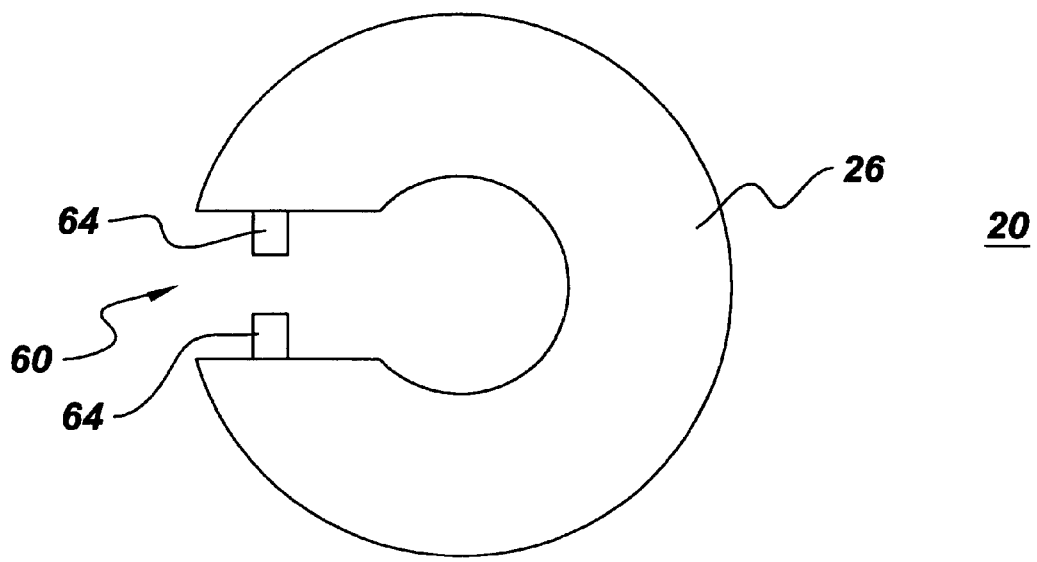
FIG. 11 depicts the beam controller fitted with a variable size aperture, in side view.
Figure 12:
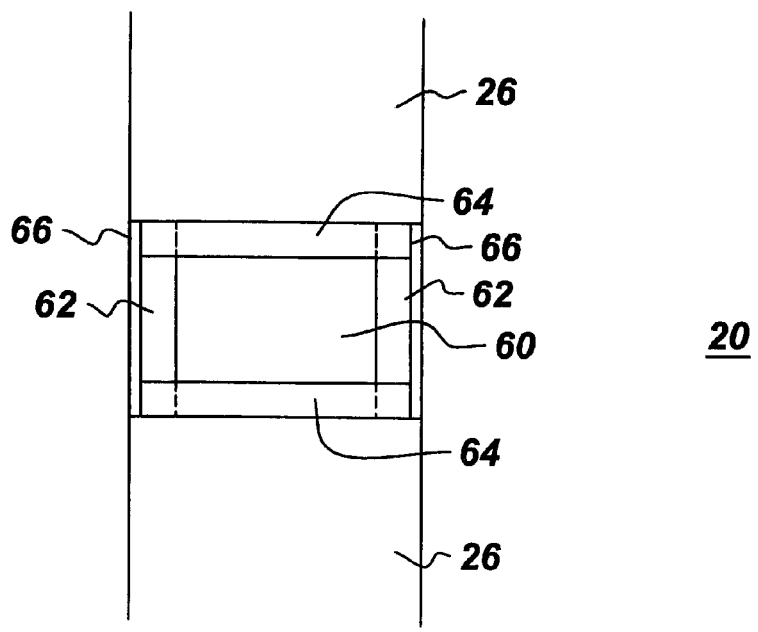
FIG. 12 is a front view of the beam controller of FIG. 12.
Figure 13:
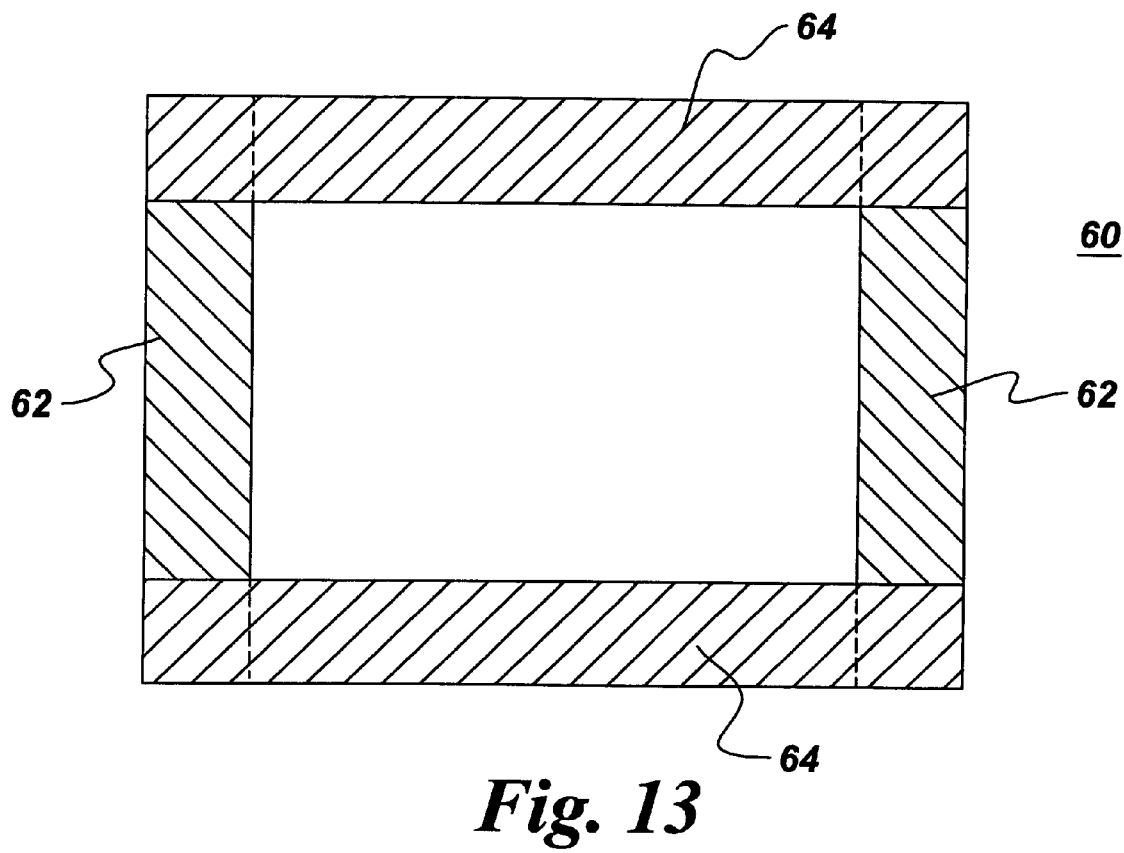
FIG. 13 shows an exemplary variable size aperture in front view in an open position.
Figure 14:
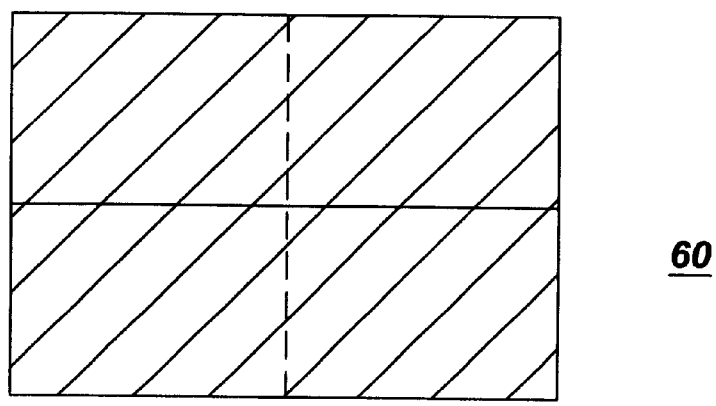
FIG. 14 shows the variable size aperture of FIG. 14 in a closed position.

Exemplary beam controllers 20 fitted with variable size apertures 60 are illustrated in FIGS. 11–14 and include a pair of horizontal shutters 62 and a pair of vertical shutters 64 that are adapted to block x-rays emitted by the source. The shutters define the variable size aperture. Exemplary vertical shutters extend from the source shield 26, as shown in FIGS. 11 and 12. As used herein, the term "extends" encompasses extending directly and indirectly (e.g., through intermediate parts, which are not shown) from the source shield. Exemplary horizontal shutters are shown in FIGS. 12–14 and, for example, extend from rails 66, as shown in FIG. 12. The rails are attached to the source shield by conventional means.

The horizontal and vertical shutters are configured to open (for example, as shown in FIG. 13) and to shut (FIG. 14), using known means such as a motor. In this manner, the aperture size can be selected to accommodate a variety of distances between the x-ray source 30 and the detector 50 (i.e., a variety of component radii R), as well as a variety of detector dimensions. Preferably, the shutters are formed from a high density, high atomic number material, such as lead, tungsten, depleted uranium, or combinations thereof, in order to block or absorb incident x-rays.

Figure 6:
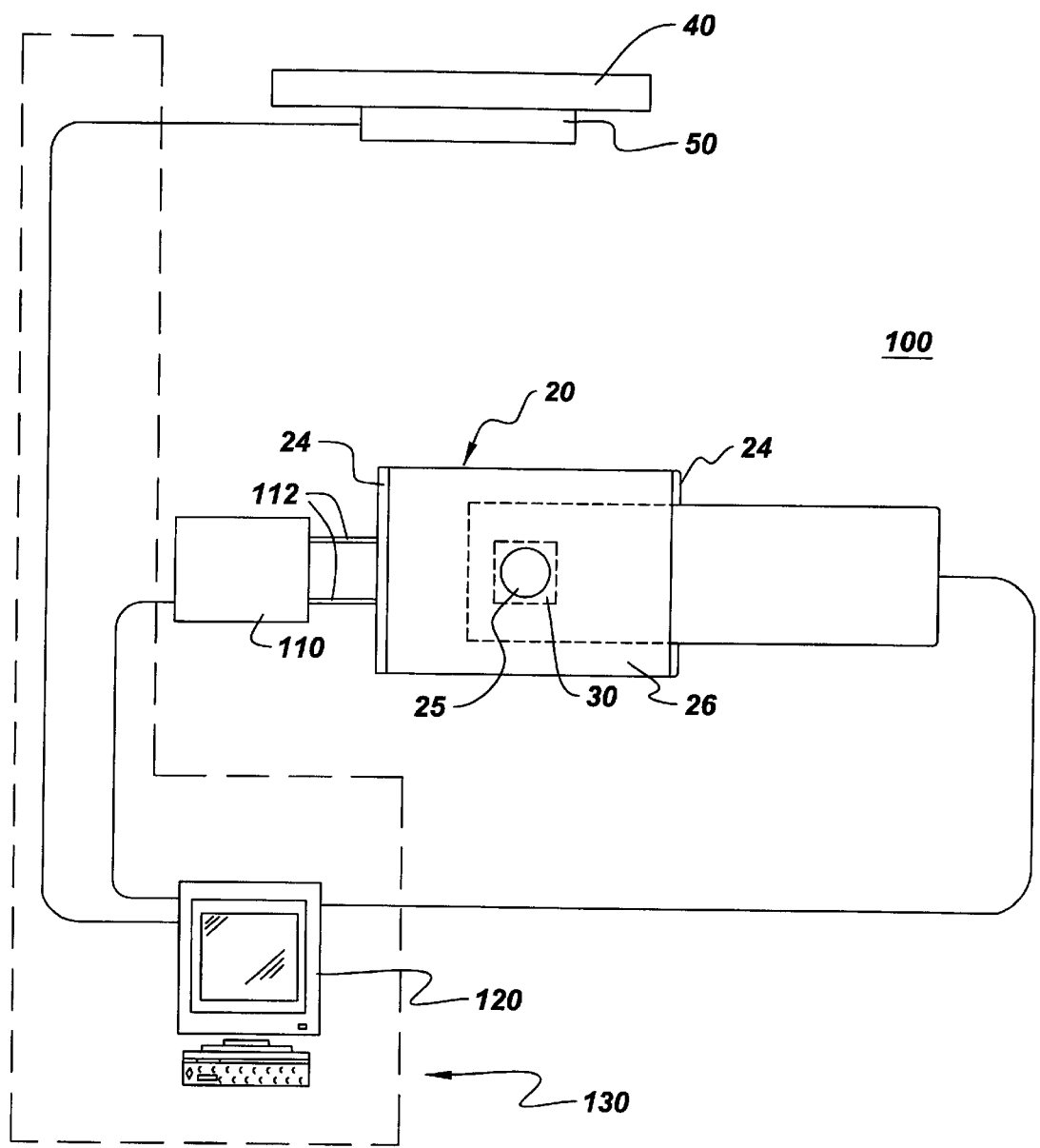
FIG. 6 shows an exemplary shielded digital radiographic inspection system embodiment of the invention.

A shielded digital radiographic inspection system 100 incorporates the x-ray shielding system 10, as illustrated in FIG. 6. Accordingly, detailed descriptions of elements discussed above are not repeated and like elements are identified with the same reference numerals.

The shielded digital radiographic inspection system 100 includes the x-ray source 30, as schematically indicated in FIG. 6. An exemplary x-ray source is a panoramic x-ray tube powered by a high voltage power supply (not shown). Panoramic x-ray tubes emit a broad angular distribution of x-rays, permitting exposure of a wide area of a hollow component, such as an aircraft fuselage, using a stationary x-ray source. By thus eliminating the need to move the x-ray source around the hollow component, the possibility of operator exposure to harmful x-rays is reduced, while reducing the overall inspection time. The panoramic x-ray tube is cited by way of example, and other x-ray sources producing a broad or narrow angular distribution of x-rays can be used.

The shielded digital radiographic inspection system 100 further includes the beam controller 20, which surrounds the x-ray source 30. The beam controller includes the source shield 26 and the aperture 25, which are discussed above with respect to the first embodiment. To permit adjustment of the collimation of the radiation field 35, the aperture is the variable size aperture 60. According to this embodiment, the beam controller further includes the pair of horizontal shutters 62 and the pair of vertical shutters 64.

The beam controller 20 is configured to rotate the aperture 25 around the x-ray source 30, as illustrated in FIG. 5. For example, the beam controller 20 can be configured to rotate around the x-ray source 30. Exemplary rotation means are discussed above with respect to the first embodiment. Alternatively, the beam controller is fixed to the x-ray source, and the beam controller and the x-ray source are collectively rotatably mounted, for producing the rotating radiation field 35 shown in FIG. 5. According to a specific embodiment, the inspection system further includes a motor 110, as schematically indicated in FIG. 6. The motor is configured to rotate the beam controller relative to the x-ray source, for the first configuration, and to rotate the beam collector and the x-ray source collectively according to the second configuration. As schematically indicated in FIG. 6, the motor is connected to the beam controller by one or more connectors 112. Exemplary connectors include rods, shafts, couplings, and screws. Alternatively, the motor can be connected to the x-ray source for collectively rotating the beam controller and the x-ray source. Advantageously, the aperture can be used to automatically scan an annular region 80 of a hollow component (also indicated by reference numeral 80) such as an aircraft fuselage, without requiring operator intervention, thereby reducing the possibility of operator exposure to radiation and increasing overall inspection speed.

Figure 9:
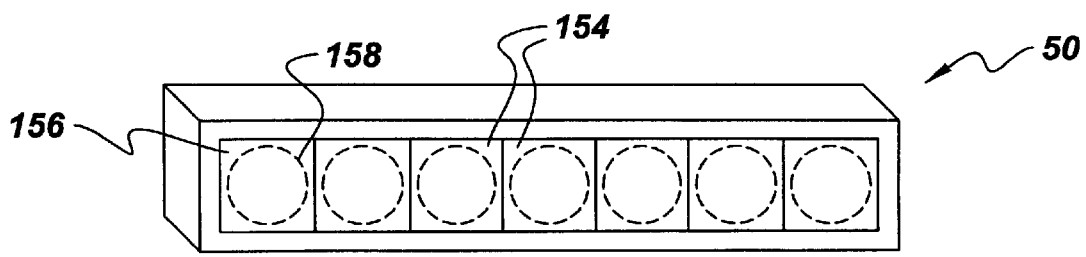
FIG. 9 is a perspective view of a linear array embodiment of a digital x-ray detector.
Figure 10:
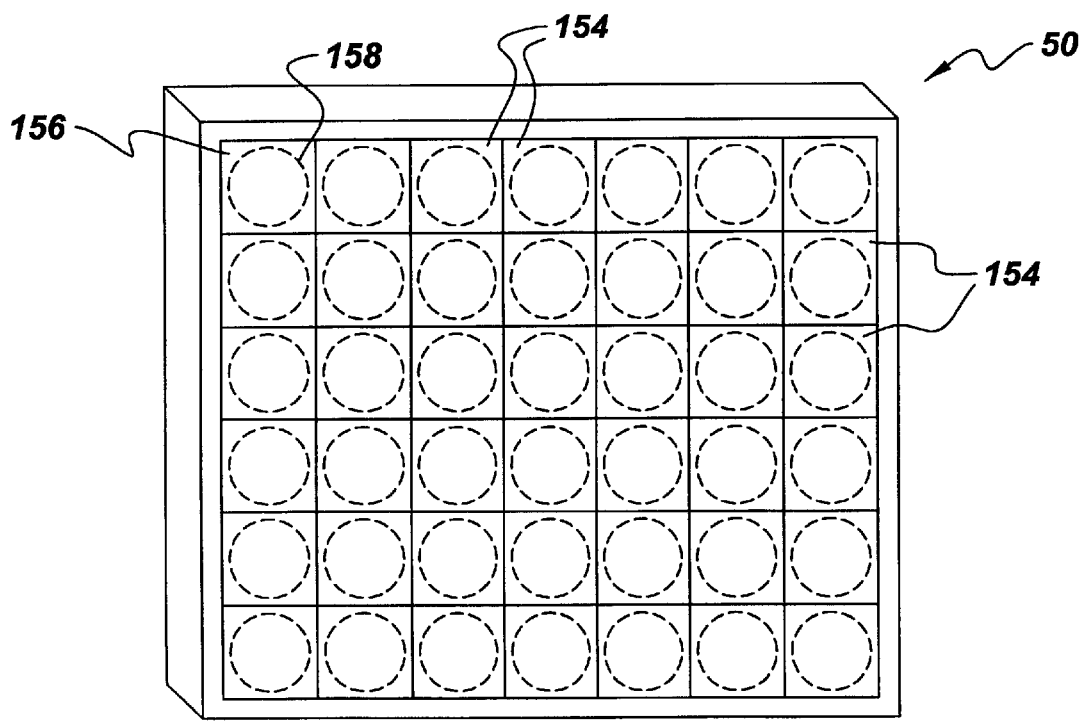
FIG. 10 is a perspective view of an area array embodiment of the digital x-ray detector.

The shielded digital radiographic inspection system 100 further includes the digital x-ray detector 50 positioned radially outward from the x-ray source and facing the aperture, as shown in FIG. 1. Exemplary digital x-ray detectors are illustrated schematically in FIGS. 9 and 10. As is known in the art, digital x-ray detectors generally have an array of cells 154, each cell 154 including a layer of x-ray sensitive material 156, such as phosphor, and an electronic means 158, such as a photodiode and transistor, located beneath the x-ray sensitive material 156 for producing an output signal that is indicative of the x-rays impinging on the x-ray sensitive material. Digital x-ray detectors are configured as either a linear array (FIG. 9) or an area array (FIG. 10). An exemplary array has a width of at least about 20 cm. However, the desired array width varies depending on the particular hollow component being inspected. An exemplary digital x-ray detector 50 is about 20 cm by about 25 cm. The digital x-ray detector is configured to be movable along an orbit 70 around the x-ray source 30, and exemplary means for moving the digital x-ray detector around the orbit are discussed above with respect to the first embodiment.

The shielded digital radiographic inspection system 100 further includes the detector shield 40, which is configured to be movable with the digital x-ray detector 50 and is positioned behind the digital x-ray detector. The detector shield is discussed above with respect to the first embodiment, including exemplary materials and dimensions.

According to a specific embodiment, the shielded digital radiographic inspection system 100 further includes a manipulator subsystem 130 for controlling rotation of the aperture 25 and for controlling movement of the digital x-ray detector 50 and the detector shield 40 along the orbit 70. An exemplary manipulator subsystem includes a processor 120, such as a computer as shown in FIG. 6. The processor is configured to initiate a rotation of the aperture 25 and to initiate motion of the digital x-ray detector and the detector shield along the orbit. For example, the processor outputs a start signal, either in accordance with preprogrammed software or with a user command input to the processor. An exemplary processor is also configured to initiate imaging by outputting a start-imaging signal to the digital x-ray detector. The exemplary processor is further configured to receive, process, and store image data signals output by the digital x-ray detector.

To rotate the aperture 25, the manipulator subsystem 130 further includes the motor 110, as schematically indicated in FIG. 6. Exemplary motors are a stepper motor and a servo motor. Upon receipt of the start signal from the processor 120, the motor rotates the aperture. In response to a stop signal received from the processor, the motor stops rotating.

More particularly, the manipulator subsystem 130 is configured to synchronize rotation of the aperture 25 with the motion of the digital x-ray detector 50 and the detector shield 40 along the orbit 70, as illustrated in FIG. 5. Here, the term "synchronized" is used to mean that the aperture faces the digital x-ray detector during imaging. Rotation of the aperture can be synchronized with the motion of the digital x-ray detector and the detector shield in a number of ways. For example, a speed of the motor 110 can be selected such that the aperture continuously faces the digital x-ray detector 50 throughout its rotation.

Alternatively, the aperture 25 and the digital x-ray detector 40 can advance between respective imaging positions 71 (see FIG. 5) at different rates. However, the processor 120 outputs a start imaging signal to the x-ray source 30 and to the digital x-ray detector only after both the aperture and the digital x-ray detector have reached the imaging positions. In this manner, the aperture faces the digital detector 40 during imaging.

Figures 7, 8:
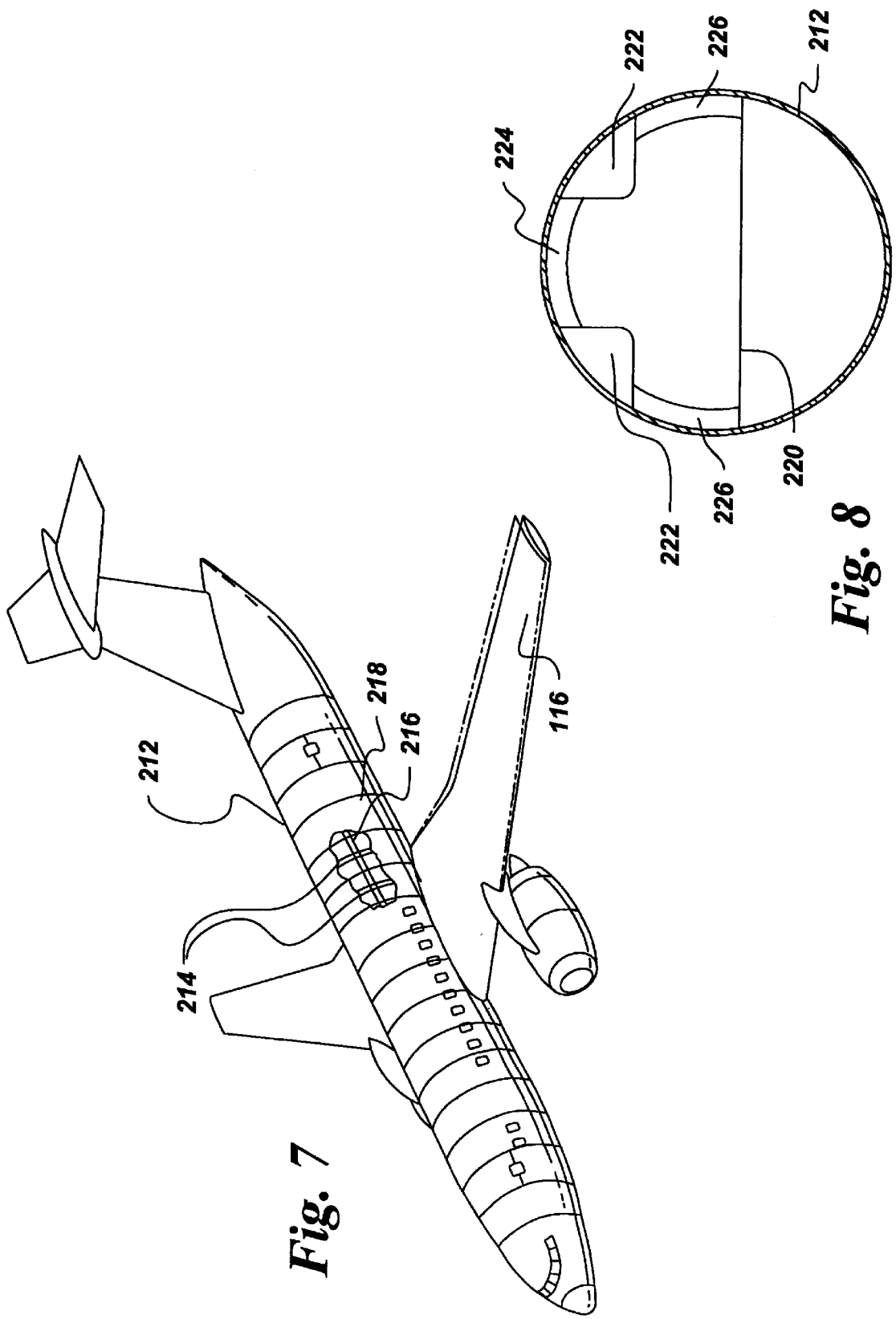
FIG. 7 is a perspective view of an aircraft having a portion of the fuselage shown in partial cutaway to reveal internal fuselage structure.
FIG. 8 is a side view of the aircraft fuselage of FIG. 7.

According to a method embodiment of the invention, a shielded digital radiographic inspection method is provided for imaging an aircraft component 212. One aircraft component of interest is an aircraft fuselage (also indicated by reference number 212), which is shown in FIG. 7 in partial cutaway view. As is known in the art, the fuselage 212 generally comprises a cylindrical wall made up of a grid of circumferential frame members 214 and longitudinal stringers 216 (shown in cutaway in FIG. 7) covered by a skin 218 of lightweight sheet metal. As seen in FIG. 8, a passenger deck 220 is disposed horizontally in the fuselage 212 so as to define the floor of an interior cabin. The cabin can be provided with conventional overhead bins 222, ventilation panels 224 and side panels 226. Although not shown in FIGS. 7 and 8, the fuselage 212 typically includes other conventional structure such as lights, wiring, insulation and the like. The wings of the aircraft are indicated by reference numeral 116.

The shielded digital radiographic inspection method includes surrounding the x-ray source 30 with the beam controller 20 to produce a collimated x-ray beam 35 through the aperture 25 of the beam controller, as shown in FIG. 1. As the inspection method employs the elements of the x-ray shielding system 10 and the inspection system 100, detailed descriptions of elements discussed above will not be repeated and like elements will be identified with the same reference numerals.

The shielded digital radiographic inspection method further includes shielding a back side 54 of the digital x-ray detector 50, as shown in FIG. 1. The digital x-ray detector is positioned radially outward from the x-ray source 30, outside the aircraft component 212, and facing the aperture 25, as shown in FIG. 1. Advantageously, the shielding reduces x-ray flux behind the digital x-ray detector, further protecting maintenance personnel from the possibility of exposure to x-rays traveling through or past the digital x-ray detector.

The shielded digital radiographic inspection method further includes imaging a portion of the aircraft component 212. The imaging includes activating the x-ray source 30 and collecting an image with the digital x-ray detector 50. Image data signals collected by the digital x-ray detector are fed to a processor 120, such as a computer. According to one aspect, the image data signals are processed and a corresponding image is generated on a monitor (also indicated by reference number 120). An operator is then able to view the displayed image to inspect for defects. According to a second aspect, the data image signals are stored in a memory of the processor.

After the imaging is completed, the aperture 25 is rotated to a subsequent aperture orientation 72, as shown in FIG. 5. To rotate the aperture, either the beam controller is rotated around a stationary x-ray source 30, or the beam controller and the x-ray source are rotated simultaneously. The digital x-ray detector 50 is moved along an orbit around the x-ray source to a subsequent detector position 71 facing the aperture, as shown in FIG. 5. The imaging is then repeated, the aperture is rotated to a new aperture position, and the detector is moved to a new detector position and so on. In this manner, a series of images are obtained for an annular portion of the aircraft component 212.

More particularly, the rotation and motion are synchronized. As explained with respect to the first and second embodiment, there are a number of different ways of synchronizing the rotation of the aperture 25 with the motion of the detector 50. For example, the speed at which the aperture is rotated and the speed at which the digital x-ray detector moves can be selected such that the aperture faces the digital x-ray detector throughout the rotation and motion. Alternatively, the rotation and motion can be completed at different times, with the imaging being initiated after completion of both the rotation and motion, such that the aperture faces the detector during imaging.

According to a specific embodiment, the rotation of the aperture 25 and the motion of the digital x-ray detector 50 are initiated in response to a start signal received from a processor 120, such as a computer. Moreover, imaging is initiated in response to receipt by the digital x-ray detector of a start imaging signal from the processor.

In more specific embodiments, the shielded digital radiographic inspection method further includes analyzing the images obtained by the digital x-ray detector 50 using the processor 120. For example, cracks and other defects are identified, located, and quantified. According to another embodiment, the method further includes storing data in the memory of the processor, such as the identity, location, size, and quantity of cracks and other defects extracted from the images.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An x-ray shielding system comprising:
   a beam controller configured to surround an x-ray source, said beam controller including source shield and an aperture, and said beam controller being configured to rotate said aperture around the x-ray source; and
   a detector shield configured to position behind an x-ray detector, the detector being configured to be movable along an orbit around the x-ray source, said detector shield being configured to be movable with the detector around the x-ray source, and said detector shield remaining positioned behind the x-ray detector, wherein said source shield and said detector shield are adapted to block x-rays, and wherein said aperture is adapted to transmit x-rays.

2. The x-ray shielding system of claim 1, wherein said beam controller is adapted to rotate said aperture in synchronicity with the detector.

3. The x-ray shielding system of claim 1, wherein the x ray source is configured to rotate, and wherein said beam controller is fixed relative to the x-ray source and is configured to rotate with the x-ray source.

4. The x-ray shielding system of claim 1, wherein said beam controller is configured to rotate around the x-ray source and to rotate relative to the x-ray source.

5. The x-ray shielding system of claim 1, wherein said beam controller further includes a first and a second side adapted to block x-rays and configured to extend from said source shield to the x-ray source.

6. The x-ray shielding system of claim 1, wherein:
   said source shield comprises a material selected from the group consisting of lead, tungsten, depleted uranium, and combinations thereof, and
   said detector shield comprises a material selected from the group consisting of lead, tungsten, depleted uranium, and combinations thereof.

7. The x-ray shielding system of claim 1, wherein said detector shield extends at least about 10 cm beyond the detector along each edge of the detector.

8. The x-ray shielding system of claim 7, wherein said detector shield extends at least about 50 cm beyond the detector along each edge of the detector.

9. The x-ray shielding system of claim 1, wherein said source shield and said detector shield are about 0.3 cm to about 1.2 cm in thickness.

10. The x-ray shielding system of claim 9, wherein said source shield and said detector shield are about 0.3 cm to about 0.6 cm in thickness.

11. The x-ray shielding system of claim 1, wherein said aperture is so dimensioned as to transmit a radiation field that approximately coincides with an area of the detector at the detector.

12. The x-ray shielding system of claim 1, wherein said detector shield is configured for attachment to a back of the detector.

13. The x-ray shielding system of claim 1, wherein said aperture is a variable size aperture.

14. The x-ray shielding system of claim 13, wherein said beam controller further comprises a pair of horizontal shutters and a pair of vertical shutters, wherein said vertical and horizontal shutters are adapted to block x-rays, are configured to open and shut, and define said variable size aperture.

15. The x-ray shielding system of claim 14, wherein said horizontal and vertical shutters comprise a material selected from the group consisting of lead, tungsten, depleted uranium, and combinations thereof.

16. A shielded digital radiographic inspection system comprising:
   an x-ray source;
   a beam controller surrounding said x-ray source, said beam controller including a source shield and an aperture, said beam controller being configured to rotate said aperture around said x-ray source;

a digital x-ray detector positioned radially outward from said x-ray source and facing said aperture, wherein said digital x-ray detector is configured to be movable along an orbit around said x-ray source; and a detector shield configured to be movable with said digital x-ray detector and positioned behind said digital x-ray detector.

17. The shielded digital radiographic inspection system of claim 16, wherein said beam controller is configured to rotate around said x-ray source and to rotate relative to said x-ray source.

18. The shielded digital radiographic inspection system of claim 16, wherein said beam controller is fixed relative to said x-ray source and is configured to rotate with said x-ray source.

19. The shielded digital radiographic inspection system of claim 16, wherein said x-ray source comprises a panoramic x-ray tube.

20. The shielded digital radiographic inspection system of claim 16, further comprising:

a manipulator susbsystem for controlling rotation of said aperture and movement of said digital x-ray detector along the orbit.

21. The shielded digital radiographic inspection system of claim 20, wherein said manipulator subsystem includes a processor, said processor being configured to initiate a rotation of said aperture and to initiate a motion of said digital x-ray detector.

22. The shielded digital radiographic inspection system of claim 21, wherein said manipulator subsystem further includes a motor for rotating said aperture, and wherein said motor is configured to rotate said aperture in response to a start signal from said processor.

23. The shielded digital radiographic inspection system of claim 20, wherein said manipulator subsystem is configured to synchronize a rotation of said aperture with a movement of said digital x-ray detector.

24. The shielded digital radiographic inspection system of claim 16, wherein:

said source shield comprises a material selected from the group consisting of lead, tungsten, depleted uranium, and combinations thereof, and said detector shield comprises a material selected from the group consisting of lead, tungsten, and depleted uranium, and combinations thereof.

25. The shielded digital radiographic inspection system of claim 16, wherein said aperture is so dimensioned as to transmit a radiation field that approximately coincides with an area of said digital x-ray detector at said digital x-ray detector.

26. The shielded digital radiographic inspection system of claim 16, wherein said aperture is a variable size aperture.

27. The shielded digital radiographic inspection system of claim 26, wherein said beam controller further comprises a pair of horizontal shutters and a pair of vertical shutters, wherein said vertical and horizontal shutters are adapted to block x-rays, are configured to open and shut, and define said variable size aperture.

28. A shielded digital radiographic inspection method for imaging an aircraft component, said inspection method comprising:

surrounding an x-ray source with a beam controller to produce a collimated x-ray beam through an aperture of the beam controller;

shielding a back side of a digital x-ray detector to reduce x-ray flux behind the digital x-ray detector, the digital x-ray detector being positioned radially outward from the x-ray source, outside the aircraft component, and facing the aperture;

imaging a portion of the aircraft component, said imaging including activating the x-ray source and collecting an image with the digital x-ray detector;

rotating the aperture around the x-ray source to a subsequent aperture orientation; and moving the digital x-ray detector along an orbit around the x-ray source to a subsequent detector position facing the aperture, wherein said rotation of the aperture, said motion of the digital x-ray detector, and said imaging are repeated for a plurality of aperture orientations and detector positions to obtain a plurality of images of an annular portion of the aircraft component.

29. The shielded digital radiographic inspection method of claim 28, wherein said rotation of the aperture is synchronized with said motion of the digital x-ray detector.

30. The shielded digital radiographic inspection method of claim 28, wherein said rotation of the aperture and said motion of the digital x-ray detector are responsive to a start signal from a processor.

31. The shielded digital radiographic inspection method of claim 30, wherein said imaging is responsive to a start imaging signal from the processor.

32. The shielded digital radiographic inspection method of claim 31, further comprising:

analyzing the images using the processor.

* * * * *